United States Patent
Atari et al.

(10) Patent No.: US 11,801,372 B2
(45) Date of Patent: Oct. 31, 2023

(54) MICRONEEDLE ARRAY

(71) Applicants: Mishima Kosan Co., Ltd., Kitakyushu (JP); Kyushu Institute of Technology, Kitakyushu (JP)

(72) Inventors: Toshiaki Atari, Kitakyushu (JP); Masaaki Matsuo, Kitakyushu (JP); Yasunori Tashiro, Kitakyushu (JP); Masaya Hara, Kitakyushu (JP); Junji Kuroki, Kitakyushu (JP); Takahiro Ito, Iizuka (JP); Tomohiro Hikima, Iizuka (JP)

(73) Assignees: MISHIMA KOSAN CO., LTD., Kitakyushu (JP); KYUSHU INSTITUTE OF TECHNOLOGY, Kitakyushu (JP)

( * ) Notice: Subject to any disclaimer, the term of this patent is extended or adjusted under 35 U.S.C. 154(b) by 567 days.

(21) Appl. No.: 16/957,172

(22) PCT Filed: Aug. 6, 2018

(86) PCT No.: PCT/JP2018/029419
§ 371 (c)(1),
(2) Date: Jun. 23, 2020

(87) PCT Pub. No.: WO2019/130640
PCT Pub. Date: Jul. 4, 2019

(65) Prior Publication Data
US 2020/0330739 A1 Oct. 22, 2020

(30) Foreign Application Priority Data
Dec. 26, 2017 (JP) ................... 2017-249120

(51) Int. Cl.
*A61M 37/00* (2006.01)
*A61M 5/32* (2006.01)

(52) U.S. Cl.
CPC ...... *A61M 37/0015* (2013.01); *A61M 5/3286* (2013.01); *A61M 2037/003* (2013.01); *A61M 2037/0023* (2013.01)

(58) Field of Classification Search
CPC ........ A61M 37/0015; A61M 2037/003; A61M 2037/0023; A61M 5/3286;
(Continued)

(56) References Cited

U.S. PATENT DOCUMENTS

2004/0049150 A1  3/2004 Dalton et al.
2004/0186419 A1  9/2004 Cho
(Continued)

FOREIGN PATENT DOCUMENTS

CN  101879336 A  11/2010
CN  106345051 A  1/2017
(Continued)

OTHER PUBLICATIONS

International Search Report dated Oct. 2, 2018, issued in counterpart International Application No. PCT/JP2018/029419. (2 pages).
(Continued)

*Primary Examiner* — Kami A Bosworth
(74) *Attorney, Agent, or Firm* — WHDA, LLP

(57) ABSTRACT

A microneedle array to be used instead of a syringe has, at a tip side of each microneedle, two or four puncture portions disposed facing each other. The puncture portions each have a part of a side surface of each microneedle as outer surfaces, respectively, and one of the puncture portions is shorter than the other(s). A housing section capable of holding a drug is formed by inner surfaces of the puncture portions of each microneedle. The housing section opens toward the tip side and lateral directions orthogonal to an axis core of each microneedle, and has a central bottom surface at a bottom end. The inner surfaces facing each other and forming the
(Continued)

housing section of each microneedle each have a downward slope, with a width between the inner surfaces getting narrower as it goes down from tips of the respective puncture portions toward the central bottom surface.

4 Claims, 6 Drawing Sheets

(58) Field of Classification Search
CPC .. A61M 2037/0061; A61M 2037/0038; A61M 2037/0046; A61M 2037/0053; A61B 5/14514; A61B 5/150984; A61B 5/685
See application file for complete search history.

(56) References Cited

U.S. PATENT DOCUMENTS

| | | | |
|---|---|---|---|
| 2009/0131887 A1* | 5/2009 | Shiomitsu | A61M 37/0015 264/220 |
| 2012/0296280 A1 | 11/2012 | Eum | |
| 2014/0066864 A1 | 3/2014 | Eum | |
| 2015/0360018 A1 | 12/2015 | Baker et al. | |
| 2016/0106965 A1 | 4/2016 | Baker et al. | |
| 2017/0368322 A1* | 12/2017 | Kato | A61M 37/00 |
| 2020/0306517 A1* | 10/2020 | Ueno | A61M 37/0015 |

FOREIGN PATENT DOCUMENTS

| | | |
|---|---|---|
| JP | 2005-246595 A | 9/2005 |
| JP | 2012-217653 A | 11/2012 |
| JP | 2013-517889 A | 5/2013 |
| JP | 2014-176568 A | 9/2014 |
| JP | 2017-217132 A | 12/2017 |
| JP | 6261795 B1 | 1/2018 |
| WO | 2012/128363 A1 | 9/2012 |
| WO | 2016/060020 A1 | 4/2016 |
| WO | 2016/147476 A1 | 9/2016 |

OTHER PUBLICATIONS

Notification of Reasons for Refusal dated Mar. 20, 2018, issued in counterpart of Japanese Patent Application No. 2017-249120 with English Translation (8 pages).
Decision to Grant a Patent dated Jun. 26, 2018, issued in counterpart of Japanese Patent Application No. 2017-249120 with English Translation (5 pages).
Office Action dated Aug. 2, 2021, issued in counterpart CN Application No. CN201880079535.9, with English Translation. (18 pages).
Office Action dated Sep. 15, 2021, issued in counterpart IN Application No. 202047029844, with English translation. (6 pages).
Notification to Grant Patent Right dated Feb. 14, 2022, issued in counterpart CN application No. CN201880079535.9, with English Translation. (4 pages).

* cited by examiner

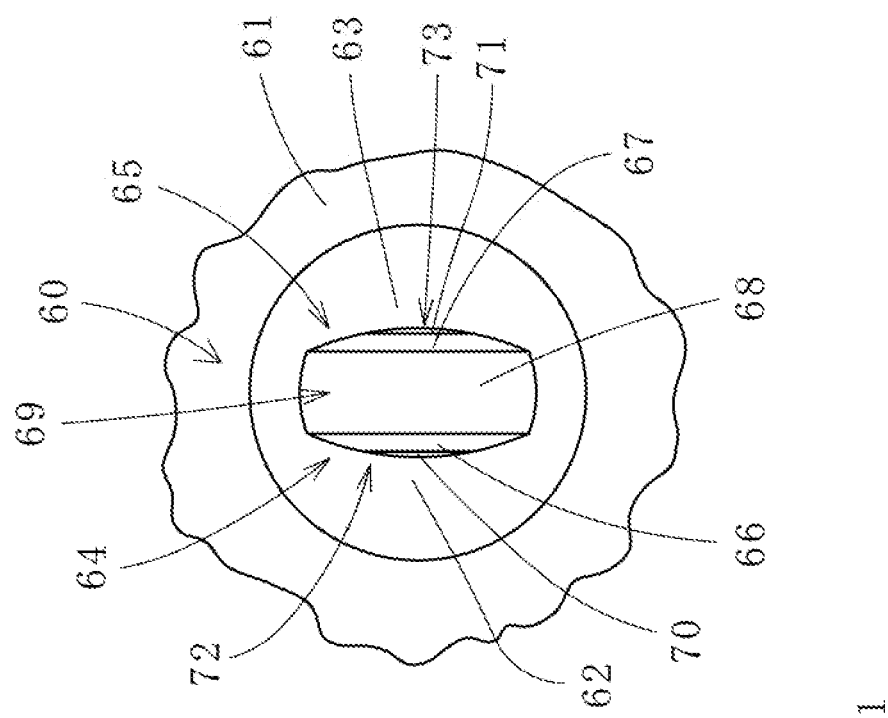
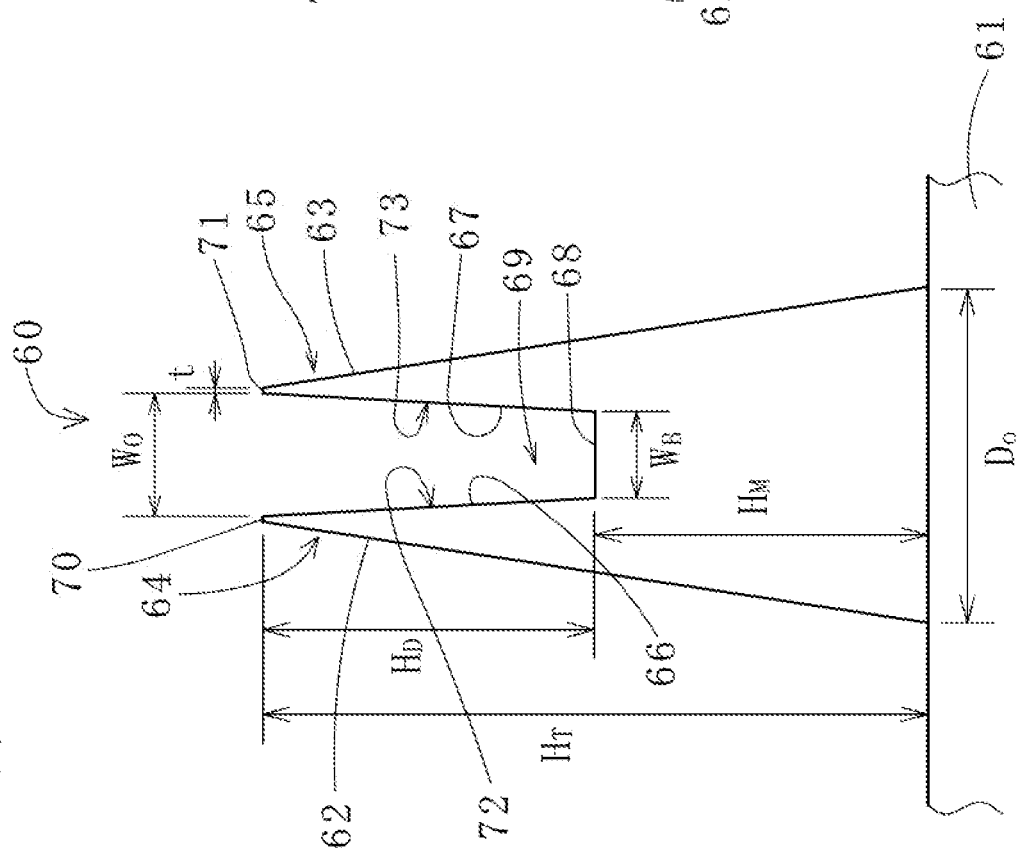
FIG. 6(A)
FIG. 6(B)

MICRONEEDLE ARRAY

TECHNICAL FIELD

The present invention is related to a microneedle array that can administer a drug into the human body replacing e.g. a syringe that is conventionally used.

BACKGROUND ART

In the future, as aging of the society progresses, the ratio occupied by medical care in the social system will increase. As a result, the needs for self-administering a drug based on a doctor's prescription will rise as one of measures to decrease the frequency of visiting the hospital for e.g. elder people and people who are too busy with their job to visit the hospital, and as part of home medical care for regions facing a shortage of doctors and/or hospitals such as an outlying area or an depopulated area.

Among medical acts, the ratio occupied by surgical procedures for affected parts such as an injury or a wound and the ratio occupied by drug administration treatments are big. Further, among the drug administration treatments, the ratio occupied by drug administration into the body with a syringe is big. Although the drug administration treatments with a syringe are usually rendered in a hospital by qualified personnel such as a doctor or a nurse, some of the treatments with a syringe are allowed to be done by patients themselves at home such as insulin administration for diabetics.

While the drug administration with a syringe has an advantage of capability to administer the drug directly under the skin or into the blood vessel, it also has disadvantages of pain at the time of inserting the needle, and scars (injection marks) or injection site swelling caused along with increase of the number of the administration.

To cope with this, there has been an idea to use instead of a syringe a microneedle array made of a resin having on a flat plate a plurality (e.g. 30 to 300/cm$^2$) of microneedles (fine needles with a diameter of e.g. 0.3 to 0.5 mm) each having a pointed tip. By making the length of each microneedle to have a size that reaches a depth of subcutaneous painless points, the pain at the time of using the microneedle array can be resolved (painless administration can be achieved). Also, since the way of use is just to put on the skin surface like a patch, the patients can easily administer the drug at home by themselves. So, using a microneedle array greatly lightens the burden on the patients.

As explained above, a microneedle array has various merits and will be significantly needed in society from now on. Thus, it is considered that if it is turned into practical use, it can greatly contribute to the aging society.

The above-mentioned microneedle array can be produced by injection molding by using e.g. molding dies disclosed by patent literature 1, more specifically molding dies having recesses formed corresponding to the shape of the microneedle array (e.g. each microneedle has a shape of a simple circular cone on a tip side). This makes it possible to mass produce the microneedle arrays at a lower cost.

CITATION LIST

Patent Literature

Patent Literature 1: Japanese Unexamined Patent Application Publication No. 2012-217653

SUMMARY OF INVENTION

Technical Problem

However, since each microneedle of the conventional microneedle array has a shape of a simple circular cone, in some cases enough amount of the drug for a predetermined amount cannot be held by the one microneedle array, and thus, a problem arises that a plurality of the microneedle arrays have to be used in order to inject a defined amount of the drug.

Additionally, since the outer diameter of each microneedle having a shape of a simple circular cone gradually expands from the tip side toward the base side, the resistance force by the skin to the microneedles increases as the microneedles are inserted deeper into the skin. So, there is a problem of difficulty for sticking the microneedle array into the skin.

In results, the microneedle array with the conventional shape did not possess adequate functions to be used instead of a syringe.

The present invention has been made in consideration of the above circumstances, and has as its object to provide a microneedle array capable of easily injecting a defined amount of a drug under the epidermis instead of a syringe.

Solution to Problem

In order to achieve the above object, a microneedle array according to a first aspect of the present invention includes:
  a plurality of frustoconical tapering microneedles made of a resin, the microneedles standing and being disposed in a dispersion state on a mount,
  wherein at a tip side of each microneedle two puncture portions facing each other are provided, the two puncture portions each have a part of a side surface of the microneedle as an outer surface, one of the two puncture portions is shorter than the other, a housing section capable of holding a drug is formed being surrounded by inner surfaces of the two puncture portions facing each other, the housing section opens toward the tip side and both lateral directions along an axis core of the microneedle, and the housing section has a central bottom surface at a bottom end,
  further wherein the inner surfaces facing each other and forming the housing section each have a downward slope, and a width between the inner surfaces gets narrower as it goes down from tips of the puncture portions toward the central bottom surface.

A microneedle array according to a second aspect of the present invention includes:
  a plurality of frustoconical tapering microneedles made of a resin, the microneedles standing and being disposed in a dispersion state on a mount,
  wherein at a tip side of each microneedle four puncture portions are provided at positions where the microneedle is evenly divided into four in a circumferential direction when viewed from above, the four puncture portions each have a part of a side surface of the microneedle as an outer surface, at least one of the four puncture portions has a different height from the other three puncture portions, a housing section capable of holding a drug is formed among the four puncture portions, the housing section opens toward the tip side and lateral directions along an axis core of the microneedle, and the housing section has a central bottom surface at a bottom end, further wherein inner surfaces facing each other of the four puncture portions forming the housing section each have a downward slope, and a width between the inner surfaces gets narrower as it goes down from tips of the puncture portions toward the central bottom surface.

As for the microneedle array according to the first and second aspects of the present invention, it is preferred that the maximum difference of the heights of the puncture portions be within a range of 0.01 to 0.4 times the height of the highest puncture portion. Employing this configuration makes it possible to prevent breakages by suppressing the occurrence of an extreme deformation of the highest puncture portion when pushing the microneedles into the skin.

As for the microneedle array according to the first and second aspects of the present invention, it is recommended that the height of the puncture portions be 1 mm at highest, preferably be 0.3 to 0.6 mm. Employing this configuration enables the pain at the time of using the microneedle array to be not felt (enables the pain to be more difficult to be felt) by having the tips of the puncture portions present at subcutaneous painless points (within a painless range) during the use.

As for the microneedle array according to the first and second aspects of the present invention, it is preferred that the angle of the downward slope of the inner surfaces of the puncture portions be within a range of 1 to 15 degrees with respect to the axis core of the microneedle. Employing this configuration enables to secure the puncturability and strength of the puncture portions. Also, employing this configuration makes it possible to suppress the occurrence of an excessive deformation of the highest puncture portion when pushing the microneedles into the skin, thereby preventing breakages.

Additionally, as for the microneedle array according to the first and second aspects of the present invention, it is preferred that the central bottom surface be flat, so that the amount of the drug to be kept by the housing section can be secured.

As for the microneedle array according to the first and second aspects of the present invention, it is preferred that the number of the puncture portions be two or four and the puncture portions be evenly arranged on the circumference of the microneedle. Employing this configuration enables the reaction force applied from the skin when the puncture portions are inserted to the skin to be evenly shared by all the puncture portions, thereby preventing breakages by suppressing uneven deformations of the puncture portions.

Incidentally, as for the microneedle array according to the first or second aspects of the present invention, it is preferred that the tips of the puncture portions of each microneedle be not pointed but non-flat or flat.

Advantageous Effects of Invention

As for the microneedle array according to the present invention, the housing section for holding a drug is provided being surrounded by the inner surfaces of the two or four puncture portions that are evenly arranged, opens toward the tip side and lateral directions along the axis core of the microneedle, and has the central bottom surface. So, comparing to the housing section formed to the conventional microneedle having a tip side of a simple circular cone shape, the volume inside the housing section can be larger. Besides, when immersing the microneedles into a drug from the tip side, the air pushed out from inside the housing section by the drug having come into from the tip side of the housing section can escape away from the base side (a part having yet to be immersed into the drug) of the housing section that opens toward the lateral directions along the axis core of the microneedle, thereby having the drug surely enter into the housing section. This enables the microneedles to hold a predetermined amount of the drug.

Further, since one of the two or four puncture portions of each microneedle is higher than the other(s), when pushing the microneedle array to the skin, it is possible to apply a pressing load in a focused manner to the highest (most projecting) puncture portion among the puncture portions provided on the tip side of each microneedle, and thus, the highest puncture portion of each microneedle can be inserted into the skin. This makes it possible to fix each microneedle to the skin with the inserted puncture portion, and then the other puncture portion(s) of each microneedle can be easily inserted to the skin by continuously applying the pressing load. In results the puncturability of the microneedles can improve.

Additionally, since a plurality of, i.e. two or four of, the puncture portions are provided, the total cross-sectional area of the puncture portions of each microneedle becomes smaller comparing to the puncture portion of each conventional microneedle with a tip side of a simple circular cone shape. This makes it possible to suppress at a lower level the increase of the resistance force applied from the skin as the microneedles are gradually inserted into the skin, and thereby the microneedle array (the microneedles) can be easily inserted into the skin.

Furthermore, since the inner surfaces of each microneedle each have a downward slope from the tip to the bottom surface of each puncture portion, the gap between the inner surfaces becomes largest at a height position of the tips of the puncture portions. So, it is possible to easily have the drug enter into the tip side of the housing section when immersing the microneedles into the drug from the tip side. Besides, just by slightly pulling out the microneedles from the skin after they are inserted into the skin a gap can be formed between each inner surface and the drug. The formed gap becomes larger as the pulling-out distance of the microneedles gets longer, and this makes it possible to easily separate the drug from the housing section and keep the drug remaining inside the skin.

If making the tips of the puncture portions of each microneedle be not pointed but non-flat or flat, it becomes easier to make concave portions (depressions each having an inside surface corresponding to an outline shape of the surface of each microneedle) to be formed on a mold for injection molding used when manufacturing the microneedle array made of a resin by injection molding, and meanwhile, it becomes easier to pour a molten resin to the end portion of the concave portions (to the region where each puncture portion is to be formed). In results, it is possible to evenly form the shape of the puncture portions, thereby easily manufacturing the microneedles with a constant shape.

BRIEF DESCRIPTION OF DRAWINGS

FIG. 6(A) is a side view of the same microneedle.
FIG. 6(B) is a plan view of the same microneedle.

DESCRIPTION OF EMBODIMENTS

The embodiments of the present invention will be described next with reference to the accompanying drawings to provide a better understanding of the present invention.

Figure 1:
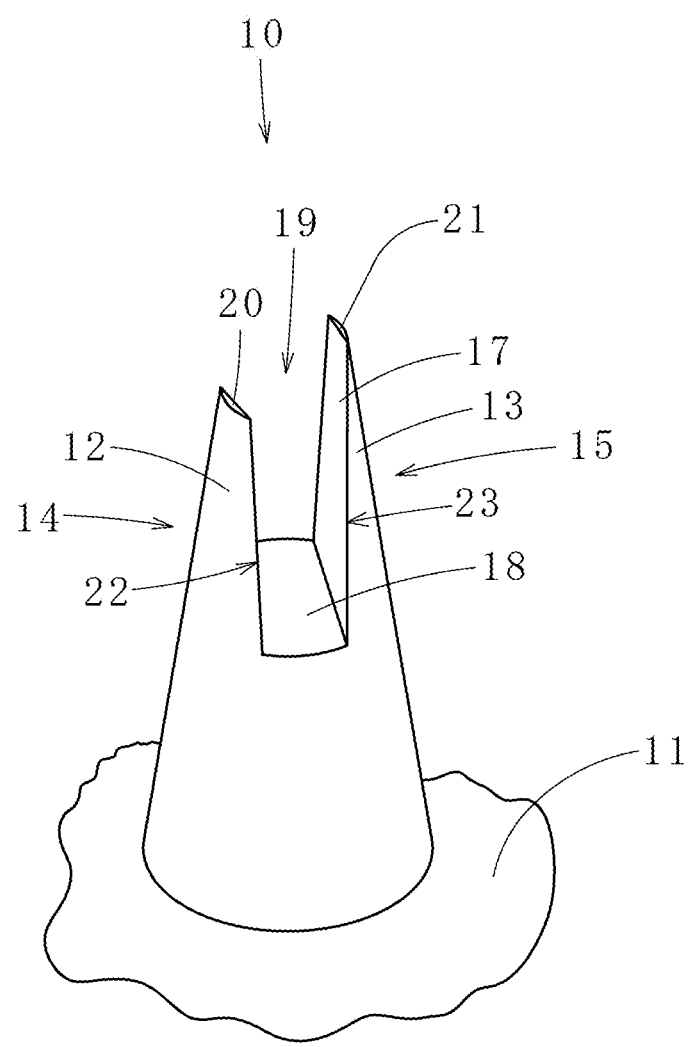
FIG. 1 is an oblique perspective figure of one of the microneedles composing the microneedle array according to a first embodiment of the present invention.
Figure 2A:
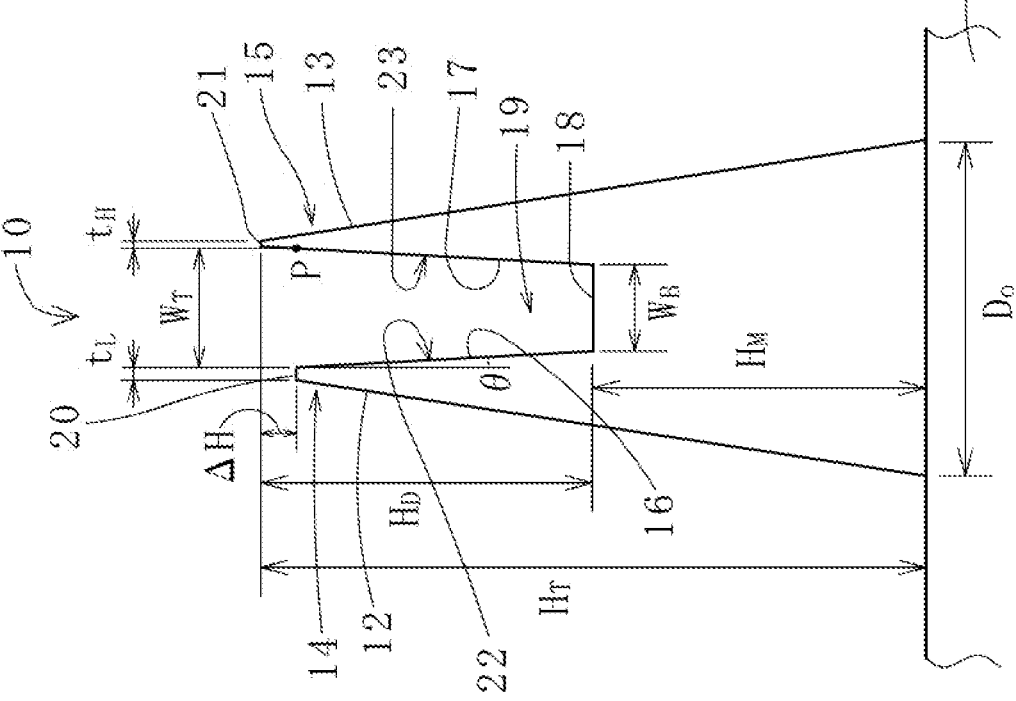
FIG. 2(A) is a side view of the same microneedle.
Figure 2B:
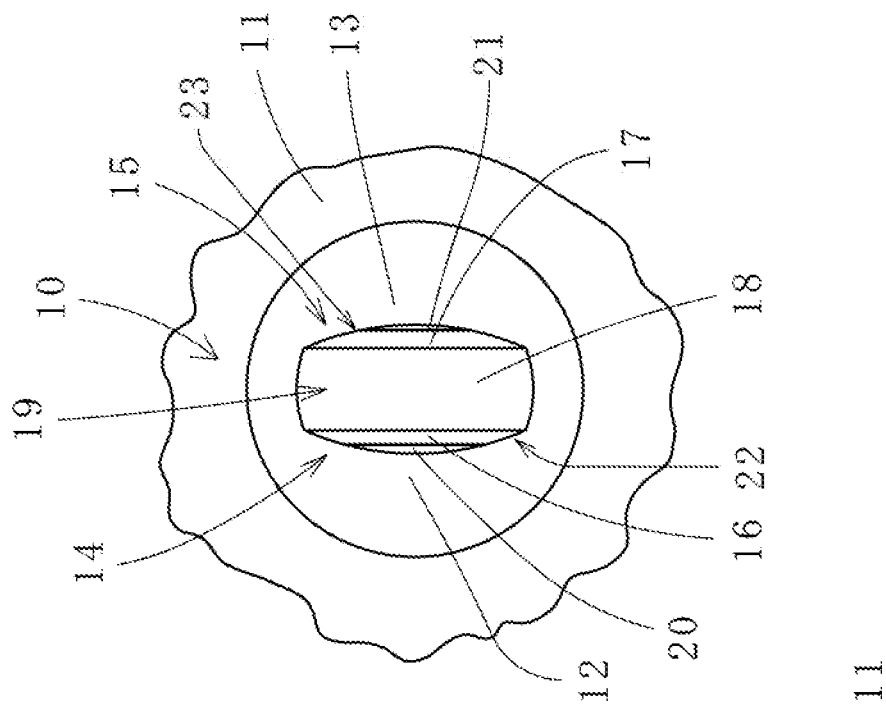
FIG. 2(B) is a plan view of the same microneedle.

As shown in FIGS. 1, 2(A), and 2(B), the microneedle array according to the first embodiment is composed by disposing in a dispersion state a plurality of microneedles (also referred to as "needles" or "fine needles") 10 made of a resin, which each are roughly in a shape of a frustum of a cone (as an example of a tapering shape), on e.g. a flat plate 11 that is an example of a mount made by using the same resin as the microneedles 10 (the microneedles 10 are standing and being disposed according to a preset arranging pattern), and it is something (a medical device) for administering a drug into the body replacing e.g. a conventionally-used syringe. A detailed explanation will be provided below.

Each microneedle 10 is provided with two puncture portions 14 and 15 facing each other each having a flat tip. The puncture portions 14 and 15 each have a part of a side surface of the microneedle 10 as an outer surface 12 and an outer surface 13, respectively (the puncture portions 14 and 15 are disposed with even spaces between each other on the circumference of the microneedle 10). Surrounded by inner surfaces 16 and 17 of the puncture portions 14 and 15, a housing section 19 capable of holding a drug is provided. The housing section 19 opens toward the tip side and lateral directions along the axis core of the microneedle 10 and has a central bottom surface (as an example of a bottom surface) 18. One of the both ends of the central bottom surface 18 is contiguous with the base end of the inner surface 16 and the other one is contiguous with the base end of the inner surface 17. The central bottom surface 18 is located on a flat surface orthogonally intersecting with the axis core of the microneedle 10 at e.g. an intermediate height position $H_M$ along the axis core direction of the microneedle 10. The height of a flat puncture portion tip surface 20 of the puncture portion 14 is shorter than that of a flat puncture portion tip surface 21 of the puncture portion 15. Incidentally, the bottom surface may not necessarily be the central bottom surface 18, and the central position of the bottom surface may be decentered from the axis core.

Here, the height of the flat puncture portion tip surface 21 of the puncture portion 15 may be made shorter than that of the flat puncture portion tip surface 20 of the puncture portion 14. Although the puncture portion tip surfaces 20 and 21 are flat in this embodiment, any one or both of the puncture portion tip surfaces of the two puncture portions may be non-flat. Moreover, although this embodiment has a configuration where the housing section has a bottom surface, it can be a configuration where the housing section does not have a bottom surface (a configuration where the base ends of the inner surfaces intersect at the bottom of the microneedle).

As shown in FIG. 2(A), the lower limit of a height $H_T$ of the microneedle 10 (the height of the puncture portion tip surface 21 of the higher puncture portion 15 with respect to the upper surface of the flat plate 11) is 0.1 mm, preferably 0.3 mm, and the upper limit of the height $H_T$ is 5.0 mm, preferably 2.0 mm. The lower limit of a base end outer diameter $D_O$ of the microneedle 10 is 0.1 mm, preferably 0.3 mm, and the upper limit of the base end outer diameter $D_O$ is 1.0 mm, preferably 0.6 mm. In a side view, the lower limit of a distance $W_T$ between the tip of the puncture portion 14 and a point P on the inner surface 17 of the puncture portion 15 that is located at the same height as the tip of the puncture portion 14 is 0.01 mm, preferably 0.1 mm, and the upper limit of the distance $W_T$ is 0.9 mm, preferably 0.3 mm.

The maximum value of a height $H_D$ of the highest puncture portion 15 (the height of the puncture portion tip surface 21) is 1 mm, preferably not shorter than 0.3 mm and not higher than 0.6 mm.

A height $H_M$ of the central bottom surface 18 (the height from the upper surface of the flat plate 11) can be decided depending on the amount of the drug to be held by the microneedle 10. The height $H_M$ is set such that the lower limit is 0.1 mm, preferably 0.3 mm, and the upper limit is 4.0 mm, preferably 1.0 mm.

The inner surfaces 16 and 17 of the housing section 19 each have a downward slope from the tips of the puncture portions 14 and 15 toward the central bottom surface 18. The side cross-sectional shape of the housing section 19 is in a trapezoidal shape (a non-isosceles trapezoidal shape) where the width gets gradually narrower from the tips of the puncture portions 14 and 15 toward the central bottom surface 18. A blade 22 of the puncture portion 14 is continuously formed along a part where the inner surface 16 and the outer surface 12 meet, whereas a blade 23 of the puncture portion is continuously formed along a part where the inner surface 17 and the outer surface 13 meet.

The volume of the housing section 19 is determined by values of the height $H_D$, the distance $W_T$, and a distance $W_B$ between the base end of the inner surface 16 of the puncture portion 14 and the base end of the inner surface 17 of the puncture portion 15. The distance $W_B$ is determined by values of the distance $W_T$ and the angle of each downward slope of the inner surfaces 16 and 17. Since the amount of the drug that the housing section 19 can hold is determined by the volume of the housing section 19, a downward slope angle θ is set within a range of 1 to 15 degrees such that the distance $W_B$ determined by the needed drug amount can be obtained. Here, it is possible to improve the puncturability of the puncture portions 14 and 15 by setting the downward slope angle θ within a range of not smaller than 1 degree and not larger than 5 degrees. Also, it is possible to improve the deformation resistance of the puncture portions 14 and 15, thereby preventing breakages by setting the downward slope angle θ beyond 5 degrees and not larger than 15 degrees. Incidentally, if the downward slope angle θ is smaller than 1 degree, it becomes more difficult to demold the microneedles from the injection mold when manufacturing the microneedles by injection molding, and if the downward slope angle θ is larger than 15 degrees, the puncturability of the microneedles declines. Thus, it is not preferred to set the downward slope angle smaller than 1 degree or larger than 15 degrees.

A difference ΔH between the heights of the puncture portion 15 (the puncture portion tip surface 21) and the puncture portion 14 (the puncture portion tip surface 20) is within a range of 0.01 to 0.4 times the height $H_D$ of the highest puncture portion 15. For example, the lower limit of the difference ΔH between the heights is 0.01 mm, preferably 0.05 mm, and the upper limit of the difference ΔH is 0.4 mm, preferably 0.2 mm. By employing this configuration, breakages of the puncture portion 15 can be suppressed, or moreover, be prevented when using the microneedle array (when the microneedles 10 are inserted into the skin).

With regard to a width $t_L$ of the puncture portion tip surface 20 (the maximum distance between the tip of the outer surface 12 and the tip of the inner surface 16) and a width $t_H$ of the puncture portion tip surface 21 (the maximum distance between the tip of the outer surface 13 and the tip of the inner surface 17), the lower limit of each width $t_L$ or $t_H$ is 0.005 mm, preferably 0.01 mm, whereas the upper limit of each width $t_L$ or $t_H$ is 0.1 mm, preferably 0.05 mm. By employing this configuration, it is possible to prevent the tip sides of the puncture portions 14 and 15 from getting deformed and broken, and besides, it is possible to maintain the puncturability of the puncture portions 14 and 15 (the tip sides of the puncture portions 14 and 15 can be easily inserted into the skin).

Table 1 shows the summary of the dimensional range and the preferred dimensional range of each part of the microneedle 10.

TABLE 1

| Item | Range of Values | Preferred Range of Values |
| --- | --- | --- |
| Height $H_T$ of the microneedle | 0.1 to 5.0 mm | 0.3 to 2.0 mm |
| Height $H_D$ of the highest puncture portion | 1 mm at largest | 0.3 to 0.6 mm |
| Height $H_M$ of the (central) bottom surface | 0.1 to 4.0 mm | 0.3 to 1.0 mm |
| Difference ΔH between the heights | 0.01 to 0.4 mm | 0.05 to 0.2 mm |
| Base end outer diameter $D_O$ of the microneedle | 0.1 to 1.0 mm | 0.3 to 0.6 mm |
| Distance $W_T$ | 0.01 to 0.9 mm | 0.1 to 0.3 mm |
| Distance $W_B$ of the (central) bottom surface | Depends on the volume of the housing section | |
| Width $t_L$ of the tip of the shorter puncture portion | 0.005 to 0.1 mm | 0.01 to 0.05 mm |
| Width $t_H$ of the tip of the higher puncture portion | 0.005 to 0.1 mm | 0.01 to 0.05 mm |
| Downward slope angle θ of the inner surfaces | 1 to 15° | For higher puncturability: 1 to 5° For improving deformation resistance: Over 5° and under 15° |

The microneedles 10 are disposed in a dispersion state e.g. by the number of 10 to 3000 or so (preferably, the lower limit is 50, the upper limit is 1000) on a range of approximately 1 cm² of the flat plate 11. Accordingly, the size of the flat plate 11 only needs to have an area on which the microneedles 10 can be arranged (The same is applicable to the embodiments below).

The shape of the area of the flat plate 11 where a plurality of the microneedles 10 to be disposed on can be decided to be an optional shape such as a rectangle, a square, a circle, an ellipse, or a polygon, when viewing the flat plate 11 from above (The same is applicable to the embodiments below), and the length of: a longer side of a rectangle, a side of a square, a diameter of a circle, a longer diameter of an ellipse, or a side of a polygon (a regular polygon) is e.g. 5 to 50 mm or so.

As a disposing pattern of a plurality of the microneedles 10 on the flat plate 11, a grid-like pattern, a staggered pattern, or a random pattern, when viewing the flat plate 11 from above, can be employed (The same is applicable to the embodiments below). Here, being arranged in a dispersion state in a staggered pattern means that when a plurality of columns each composed of the microneedles linearly arranged (while standing) with a regular space are there and any two of the columns next to each other are focused, each microneedle in one of the columns is disposed at a position corresponding to the middle of the microneedles next to each other in the other column.

Incidentally, the shape, the dimension, and the number of the microneedles 10, the way to arrange the microneedles on the flat plate 11, and the conditions about the arranging region are not limited but may be variously changed as long as they suit the use application of the microneedle array (from a perspective of e.g. the suitability with respect to the body part to which a drug is administered, and the amount of the drug to be administered) (The same is applicable to the embodiments below).

As a resin for forming the microneedles 10, e.g. a biodegradable plastic (a biodegradable resin), a thermoplastic resin, or a thermosetting resin can be used (The same is applicable to the embodiments below).

The biodegradable plastic is a plastic that is decomposed by microorganisms, and it includes e.g. polylactic acid, polycaprolactone, polyhydroxyalkanoate, polyglycolic acid, modified polyvinyl alcohol, casein, modified starch, or else. Among all, the polylactic acid is especially preferred. The polylactic acid is made by using corn as its raw material and has a characteristic of being decomposed into carbon dioxide and oxygen inside the human body and in a natural environment. Thus, by making the microneedles with polylactic acid it is harmless to the human body even when breakage of the microneedles occurs inside the body because the microneedles made of polylactic acid will be decomposed and absorbed to the body.

As a thermoplastic resin, e.g. polycarbonate resin, polyethylene resin, polypropylene resin, AS resin, ABS resin, methacrylic acid resin, polyvinyl chloride resin, polyacetal resin, polyamide resin, modified polyphenylene ether resin, polybutylene terephthalate resin, polyethylene terephthalate resin, or else can be used; however, the polycarbonate resin is preferred.

As a thermosetting resin, e.g. phenol resin, epoxy resin, melamine resin, unsaturated polyester resin, polyurethane resin, thermosetting polyimide resin, or else can be used.

Actions of the microneedle array according to the first embodiment of the present invention will subsequently be explained.

When pushing the microneedles 10 onto the skin (epidermis), since the puncture portion tip surface 21 of the puncture portion 15 is higher than (protruding from) the puncture portion tip surface 20 of the puncture portion 14, it is possible to apply a pressing load in a focused manner to the puncture portion tip surface 21 of the puncture portion 15, thereby the tip of the puncture portion 15 can be easily inserted into the skin. At the same time, a slit portion is formed on the surface layer side of the skin along the outline of the tip of the puncture portion 15.

Here, the lower limit of the difference between the heights of the puncture portion tip surface 21 of the puncture portion 15 and the puncture portion tip surface 20 of the puncture portion 14 is 0.01 times the height $H_D$ of the highest puncture portion 15, and thus, each microneedle 10 can be fixed to the skin (deviation of each microneedle 10 can be prevented) through the already inserted puncture portion 15. Also, the upper limit of the difference between the heights of the puncture portion tip surface 21 and the puncture portion tip surface 20 is 0.4 times the height of the highest puncture portion 15, and thus, the time during which only the puncture portion 15 is inserted into the skin when pushing the microneedles 10 onto the skin can be short, thereby deformation of the puncture portion 15 can be suppressed and breakage of the puncture portion 15 can be prevented. So, by continuing to apply the pressing load, the tip side of the puncture portion 14 can be inserted into the skin. At the same time, a slit portion is formed on the surface layer side of the skin along the outline of the tip of the puncture portion 14 in addition to the slit portion along the outline of the tip of the puncture portion 15.

By means of the slit portions formed on the surface layer side of the skin along the outlines of the tips of the puncture portions 14 and 15, when further pushing the microneedles 10 into the skin, a part of the skin existing between the puncture portions 14 and 15 enters into the housing section 19. This makes it possible to keep at a lower level the increase of the resistance force applied by the skin as the puncture portions 14 and 15 are gradually inserted into the skin, comparing to the conventional microneedle with a tip side of a simple circular cone shape, thereby easily inserting the microneedles 10 into the skin (possible to improve the puncturability of the microneedles 10).

Since the depth of the housing section 19 accords with the height $H_D$ of the puncture portion 15 and the difference ΔH between the heights of the puncture portion tip surfaces 21 and 20 is within a range of 0.01 to 0.4 times the height $H_D$ of the highest puncture portion 15, both of the puncture portion tip surfaces 20 and 21 can be reach the dermis and the drug inside the housing section 19 moves to the dermis (under the epidermis), or otherwise, it is expected that the drug inside the housing section 19 is surely pushed out by the part of the skin that is entering into the housing section 19. This makes it possible to make the drug pushed out from the housing section 19 effectively reach the dermis by using the slit portions formed on the skin, especially parts of the slit portions along the inner surfaces 16 and 17 of the puncture portions 14 and 15.

The housing section 19 is formed between the puncture portions 14 and 15. So, the volume of the housing section 19 can be made larger comparing to the volume of a housing section, which is formed at a central part of the conventional microneedle having a shape of a simple circular cone and along the axis core of the conventional microneedle. Besides, when immersing the microneedles 10 into the drug from the tip side, the air pushed out from inside the housing section 19 by the drug having come into the tip side of the housing section 19 can escape away from the base side (a part having yet to be immersed into the drug) of the housing section 19 that opens toward the lateral directions along the axis core of each microneedle 10, and thus, the drug can surely enter into the housing section 19. This enables the microneedles 10 to hold the predetermined amount of the drug.

Figure 3:
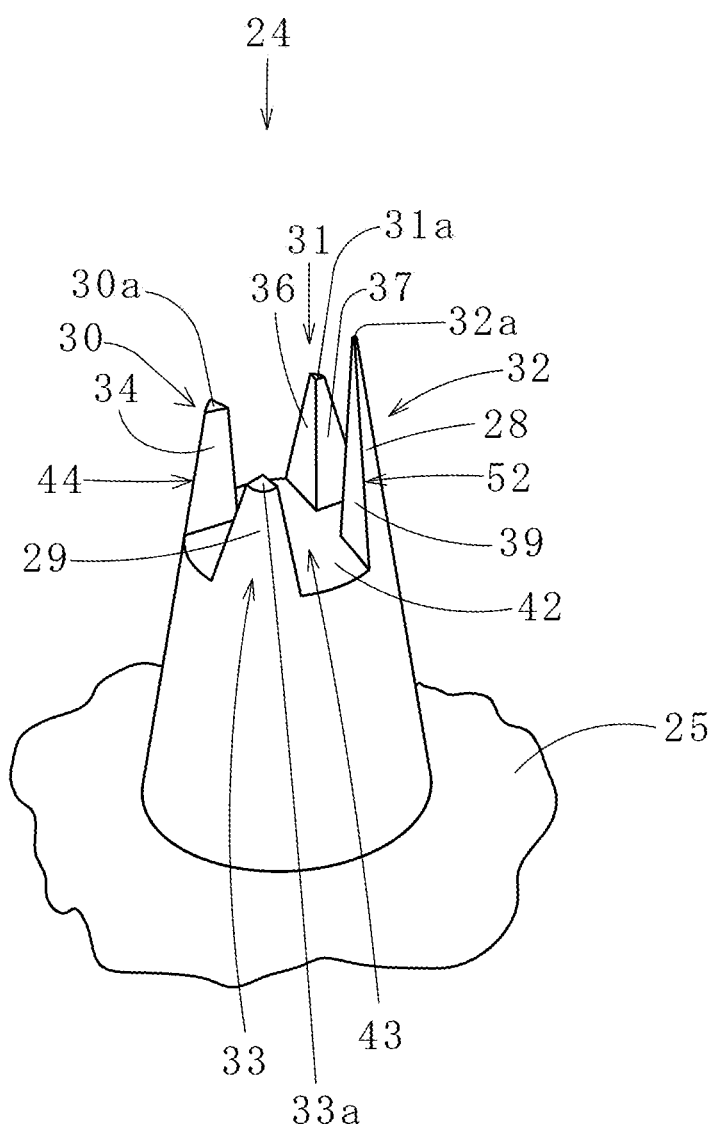
FIG. 3 is an oblique perspective figure of one of the microneedles composing the microneedle array according to a second embodiment of the present invention.
Figure 4A:
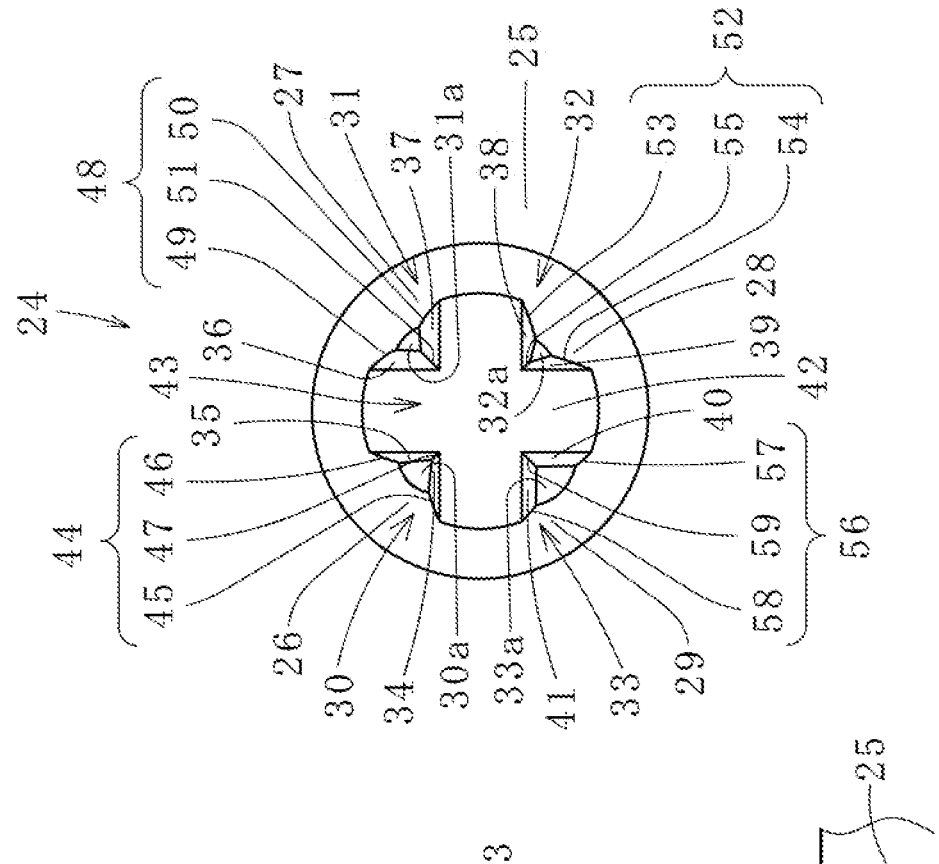
FIG. 4(A) is a side view of the same microneedle.
Figure 4B:
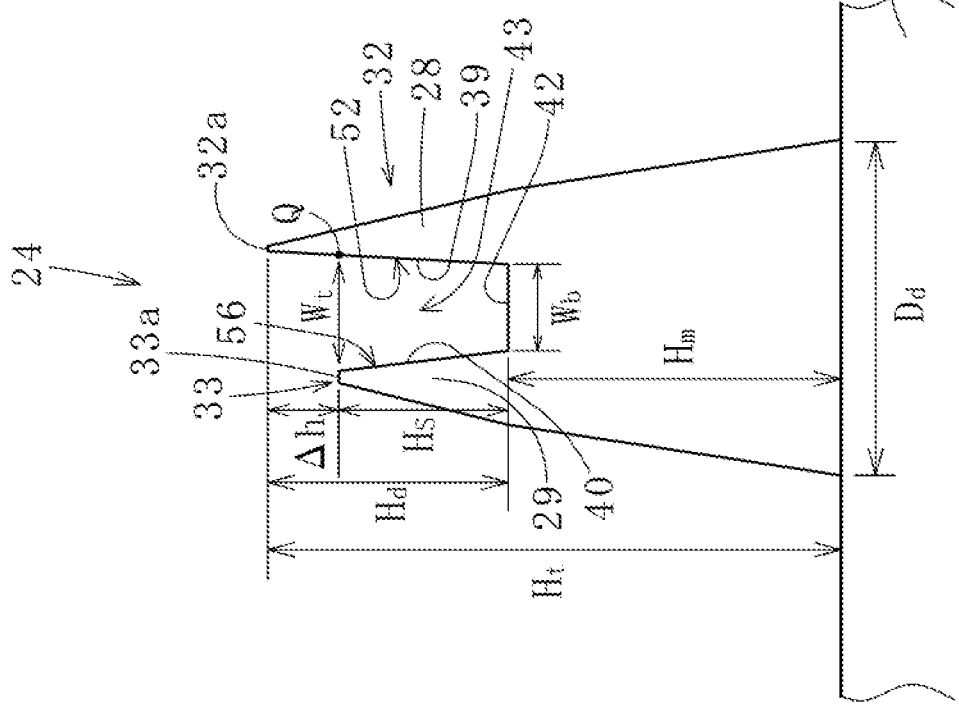
FIG. 4(B) is a plan view of the same microneedle.

As shown in FIGS. 3, 4(A), and 4(B), the microneedle array according to the second embodiment is composed by disposing in a dispersion state a plurality of microneedles (also referred to as "needles" or "fine needles") 24 made of a resin, which each are roughly in a shape of a frustum of a cone (as an example of a tapering shape), on e.g. a flat plate 25 that is an example of a mount made by using the same resin as the microneedles 24 (the microneedles 24 are standing and being disposed according to a preset arranging pattern), and it is something (a medical device) for administering a drug into the body replacing e.g. a conventionally-used syringe. Incidentally, instead of making the rough shape of each microneedle 24 be a frustum of a cone, it may be made to be a frustum of e.g. an elliptic cone or a polygonal pyramid (a triangular pyramid, a quadrangular pyramid, or else). A detailed explanation will be provided below.

Each microneedle 24 is provided with four puncture portions 30, 31, 32, and 33 each having a flat tip. The puncture portions 30, 31, 32, and 33 each have a part of a side surface of the microneedle 24 as outer surfaces 26, 27, 28, and 29, respectively. The puncture portions 30, 31, 32, and 33 are provided surrounding the axis core of the microneedle 24, and their puncture directions accord with the direction of the axis core of the microneedle 24. The puncture portions 30, 31, 32, and 33 are evenly spaced on the circumference of the microneedle 24 (disposed at circumferential angle positions where the circumference is evenly divided into four along a circumferential direction) when viewing the microneedle 24 from above. With the axis core of the microneedle 24 in between, the puncture portions 30 and 32 face to each other, while the puncture portions 31 and 33 face to each other.

Incidentally, it can be also three puncture portions evenly spaced on the circumference of the microneedle (disposed at circumferential angle positions where the circumference is evenly divided into three along a circumferential direction) when viewing the microneedle from above to be provided to each microneedle. Moreover, it can be also three or four puncture portions unevenly spaced on the circumference of the microneedle when viewing the microneedle from above to be provided to each microneedle.

The puncture portion 30 has a pair of inner surfaces 34 and 35 intersecting (meeting each other) on the axis core side of the microneedle 24. The puncture portion 31 has inner surfaces 36 and 37 intersecting on the axis core side of the microneedle 24. The puncture portion 32 has inner surfaces 38 and 39 intersecting on the axis core side of the microneedle 24. The puncture portion 33 has inner surfaces 40 and 41 intersecting on the axis core side of the microneedle 24. The microneedle 24 is provided with a housing section 43 capable of holding a drug. The housing section 43 is surrounded by the inner surfaces 34 to 41 of the puncture portions 30 to 33 facing toward the axis core of the microneedle 24. The housing section 43 opens toward the tip side and lateral directions along the axis core of the microneedle 24 and has a central bottom surface 42 that is an example of a bottom surface. Here, the central bottom surface 42 is contiguous with every base end of the inner surfaces 34 to 41 and is located on a flat surface orthogonally intersecting (as an example of intersecting) with the axis core of the microneedle 24 at e.g. an intermediate height $H_m$ along the axis core direction of the microneedle 24. Moreover, although this embodiment has a configuration where the housing section 43 has a bottom surface (e.g. the central bottom surface 42), it can be a configuration where the housing section does not have a bottom surface. Also, in this embodiment the puncture portions 30 to 33 each have a different height and their heights get higher in order of the puncture portion 33, the puncture portion 30, the puncture portion 31, and the puncture portion 32; however, it is sufficient that at least one of their heights differs from the others among the four puncture portions 30 to 33. Additionally, although all of tip surfaces 30a, 31a, 32a, and 33a of the four puncture portions 30 to 33 are flat, it may be that at least one tip surface is flat and the others are non-flat or all the tip surfaces are non-flat among the tip surfaces of the four puncture portions.

In a case where the number of the puncture portions is three, it may be that at least one tip surface is flat and the others are non-flat or all the tip surfaces are non-flat among tip surfaces of the three puncture portions.

As shown in FIG. 4(A), the lower limit of a height $H_t$ of the microneedle 24 (the height of the highest tip surface 32a with respect to the upper surface of the flat plate 25) is 0.1 mm, preferably 0.3 mm. The upper limit of the height $H_t$ is 5.0 mm, preferably 2.0 mm. The lower limit of a base end outer diameter $D_d$ of the microneedle 10 is 0.1 mm, preferably 0.3 mm, and the upper limit of the base end outer diameter $D_d$ is 1.0 mm, preferably 0.6 mm.

In a side view, the lower limit of a distance $W_t$ between the tip surface 33a of the shortest puncture portion 33 and a point Q on the inner surface 39 of the highest puncture portion 32 that is located at the same height as the tip surface 33a is 0.01 mm, preferably 0.1 mm, and the upper limit of the distance $W_t$ is 0.9 mm, preferably 0.3 mm. The maximum value of a height $H_d$ of the highest puncture portion 32 is 1 mm, preferably not shorter than 0.3 mm and not higher than 0.6 mm. Thus, a height $H_m$ of the central bottom surface 42 (the height from the upper surface of the flat plate 11) can be decided depending on the amount of the drug to be held by the microneedle 24. The height $H_m$ is set such that the lower limit is 0.1 mm, preferably 0.3 mm, and the upper limit is 4.0 mm, preferably 1.0 mm.

The inner surfaces 35 and 36 facing each other of the side-by-side puncture portions 30 and 31 each have a downward slope from the tips of the puncture portions 30 and 31 toward the central bottom surface 42 in a side view. The side cross-sectional shape of the area between the inner surfaces 35 and 36 facing each other (a part of the housing section 43) is in a trapezoidal shape (a non-isosceles trapezoidal shape) where the width gets gradually narrower from the tips of the puncture portions 30 and 31 toward the central bottom surface 42.

The inner surfaces 37 and 38 facing each other of the side-by-side puncture portions 31 and 32 each have a downward slope from the tips of the puncture portions 31 and 32 toward the central bottom surface 42 in a side view. The side cross-sectional shape of the area between the inner surfaces 37 and 38 facing each other (a part of the housing section 43) is in a trapezoidal shape (a non-isosceles trapezoidal shape) where the width gets gradually narrower from the tips of the puncture portions 31 and 32 toward the central bottom surface 42.

The inner surfaces 39 and 40 facing each other of the side-by-side puncture portions 32 and 33 each have a downward slope from the tips of the puncture portions 32 and 33 toward the central bottom surface 42 in a side view. The side cross-sectional shape of the area between the inner surfaces 39 and 40 facing each other (a part of the housing section 43) is in a trapezoidal shape (a non-isosceles trapezoidal shape) where the width gets gradually narrower from the tips of the puncture portions 32 and 33 toward the central bottom surface 42.

The inner surfaces 41 and 34 facing each other of the side-by-side puncture portions 33 and 30 each have a downward slope from the tips of the puncture portions 33 and 30 toward the central bottom surface 42 in a side view. The side cross-sectional shape of the area between the inner surfaces 41 and 34 facing each other (a part of the housing section 43) is in a trapezoidal shape (a non-isosceles trapezoidal shape) where the width gets gradually narrower from the tips of the puncture portions 33 and 30 toward the central bottom surface 42.

A blade 44 of the puncture portion 30 includes a partial blade 45, a partial blade 46, and a partial blade 47. The partial blade 45 is continuously formed along a part where the inner surface 34 and the outer surface 26 meet, the partial blade 46 is continuously formed along a part where the inner surface 35 and the outer surface 26 meet, and the partial blade 47 is continuously formed along a part where the inner surfaces 34 and 35 meet.

A blade 48 of the puncture portion 31 includes a partial blade 49, a partial blade 50, and a partial blade 51. The partial blade 49 is continuously formed along a part where the inner surface 36 and the outer surface 27 meet, the partial blade 50 is continuously formed along a part where the inner surface 37 and the outer surface 27 meet, and the partial blade 51 is continuously formed along a part where the inner surfaces 36 and 37 meet.

A blade 52 of the puncture portion 32 includes a partial blade 53, a partial blade 54, and a partial blade 55. The partial blade 53 is continuously formed along a part where the inner surface 38 and the outer surface 28 meet, the partial blade 54 is continuously formed along a part where the inner surface 39 and the outer surface 28 meet, and the partial blade 55 is continuously formed along a part where the inner surfaces 38 and 39 meet.

A blade 56 of the puncture portion 33 includes a partial blade 57, a partial blade 58, and a partial blade 59. The partial blade 57 is continuously formed along a part where the inner surface 40 and the outer surface 29 meet, the partial blade 58 is continuously formed along a part where the inner surface 41 and the outer surface 29 meet, and the partial blade 59 is continuously formed along a part where the inner surfaces 40 and 41 meet.

The volume of the housing section 43 is determined by values of the height $H_d$, the distance $W_t$, and a distance $W_b$ between the base ends of the inner surfaces 39 and 40 (the inner surfaces 35 and 36, the inner surfaces 37 and 38, the inner surfaces 41 and 34) facing each other. The distance $W_b$ is determined by values of the distance $W_t$ and the angle of each downward slope of the inner surfaces 39 and 40 (the inner surfaces 35 and 36, the inner surfaces 37 and 38, the inner surfaces 41 and 34). Since the amount of the drug that the housing section 43 can hold is determined by the volume of the housing section 43, the downward slope angle is set within a range of 1 to 15 degrees such that the distance $W_b$ determined by the needed drug amount can be obtained.

Here, it is possible to improve the puncturability of the puncture portions 30 to 33 by setting the downward slope angle within a range of not smaller than 1 degree and not larger than 5 degrees. Also, it is possible to improve the deformation resistance of the puncture portions 30 to 33 by setting the downward slope angle beyond 5 degrees and not larger than 15 degrees. Incidentally, if the downward slope angle is smaller than 1 degree, it becomes more difficult to demold the microneedles from the injection mold when manufacturing the microneedles by injection molding, and if the downward slope angle is larger than 15 degrees, the puncturability of the microneedles declines. Thus, it is not preferred to set the downward slope angle smaller than 1 degree or larger than 15 degrees.

A maximum difference Δh between the height $H_d$ of the puncture portion 32 and a height $H_s$ of the puncture portion 33 is within a range of 0.01 to 0.4 times the height $H_d$ of the highest puncture portion 32. By employing this configuration, breakages of the puncture portion 32 can be suppressed, or moreover, be prevented when using the microneedle array (when the microneedles 24 are inserted into the skin).

With regard to the width of each of the tip surfaces 30a, 31a, 32a, and 33a of the puncture portions 30 to 33 (the maximum distance between the tip of the pair of the inner surfaces intersecting on the axis core side of the microneedle 24 and the tip of the outer surface, with respect to each puncture portion), the lower limit of the width is 0.005 mm, preferably 0.01 mm, whereas the upper limit of the width is 0.1 mm, preferably 0.05 mm. By employing this configuration, it is possible to prevent the tip sides of the puncture portions 30 to 33 from getting deformed and broken, and besides, it is possible to maintain the puncturability of the puncture portions 30 to 33 (the tip sides of the puncture portions 30 to 33 can be easily inserted into the skin).

Actions of the microneedle array according to the second embodiment of the present invention will subsequently be explained.

When pushing the microneedles 24 onto the skin (epidermis) (when cutting slits into the skin with the blades 44, 48, 52, and 56 of the puncture portions 30 to 33), since the puncture portion 32 is higher than (protruding from) the puncture portions 30, 31, and 33, it is possible to apply a pressing load in a focused manner to the tip of the puncture portion 32, thereby the tip side of the puncture portion 32 can be easily inserted into the skin. At the same time, a slit portion is formed on the surface layer side of the skin along the outline of the tip of the puncture portion 32.

Here, the lower limit of the difference (the maximum difference) $\Delta h$ between the height $H_d$ of the puncture portion 32 and the height $H_s$ of the puncture portion 33 is 0.01 times the height $H_d$ of the highest puncture portion 32, and thus, each microneedle 24 can be fixed to the skin (deviation of each microneedle 24 can be prevented) through the already inserted puncture portion 32. Also, the upper limit of the difference $\Delta h$ is 0.4 times the height $H_d$ of the highest puncture portion 32, and thus, the time during which only the puncture portion 32 is inserted into the skin when pushing the microneedles 24 onto the skin can be short, thereby deformation of the puncture portion 32 can be suppressed and breakage of the puncture portion 32 can be prevented. So, by continuing to apply the pressing load, each tip side of the other puncture portions can be inserted into the skin in order of the puncture portions 31, 30, and 33. At each time the puncture portions 31, 30, and 33 are inserted into the skin, a slit portion is formed on the surface layer side of the skin along each outline of the tips of the puncture portions 31, 30, and 33 in addition to the slit portion along the outline of the tip of the puncture portion 32.

By means of the slit portions formed on the surface layer side of the skin along the outlines of the tips of the puncture portions 30 to 33, when further pushing the microneedles 24 into the skin, a part of the skin existing among the puncture portions 30 to 33 enters into the housing section 43. This makes it possible to keep at a lower level the increase of the resistance force applied by the skin as the puncture portions 30 to 33 are gradually inserted into the skin, comparing to the conventional microneedle with a tip side of a simple circular cone shape, thereby easily inserting the microneedles 24 into the skin (possible to improve the puncturability of the microneedles 24).

Here, the depth of the housing section 43 accords with the height $H_d$ of the highest puncture portion 32, and the maximum value of the height $H_d$ is 1 mm, preferably not shorter than 0.3 mm and not higher than 0.6 mm. The maximum difference $\Delta h$ among the heights of the puncture portions 30 to 33 is within a range of 0.01 to 0.4 times the height $H_d$ of the puncture portion 32. Thus, the drug inside the housing section 43 moves to the dermis (under the epidermis), or otherwise, it is expected that the drug inside the housing section 43 is surely pushed out by the part of the skin that is entering into the housing section 43. This makes it possible to make the drug pushed out from the housing section 43 effectively reach the dermis by using the slit portions formed on the skin, especially parts of the slit portions along the inner surfaces 34 to 41 of the puncture portions 30 to 33.

The housing section 43 is formed among the four puncture portions 30 to 33. So, the volume of the housing section 43 can be made larger comparing to the volume of a housing section, which is formed at a central part of the conventional microneedle having a shape of a simple circular cone and along the axis core of the conventional microneedle. Besides, when immersing the microneedles 24 into the drug from the tip side, the air pushed out from inside the housing section 43 by the drug having come into the tip side of the housing section 43 can escape away from the base side (a part having yet to be immersed into the drug) of the housing section 43 that opens toward the lateral directions along the axis core of the microneedle 24, and thus, the drug can surely enter into the housing section 43. This enables the microneedles 24 to hold the predetermined amount of the drug.

Figure 5:
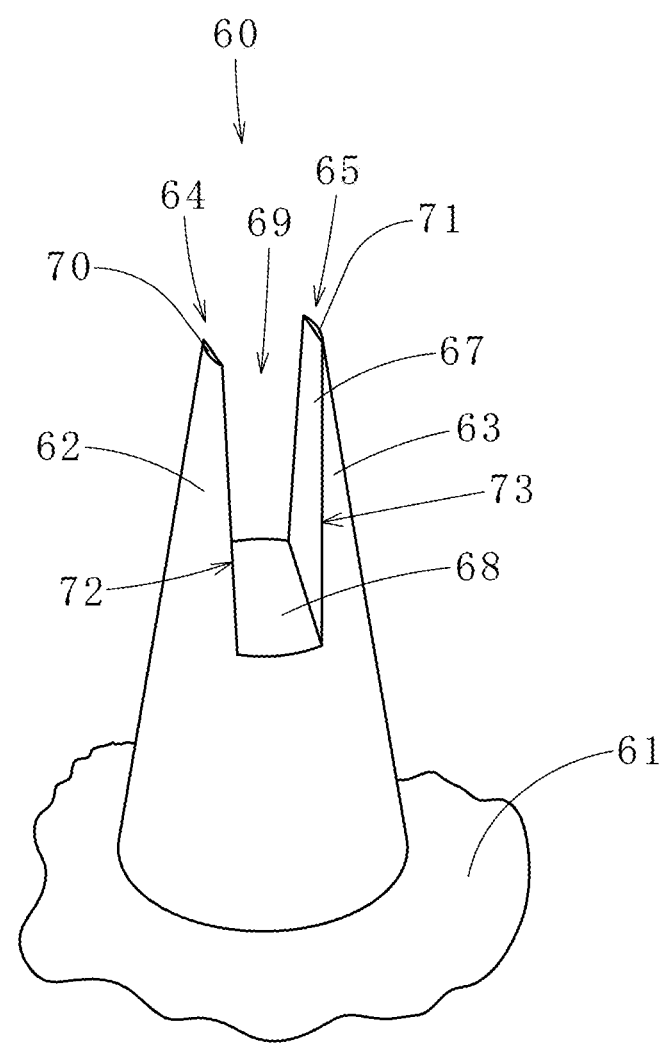
FIG. 5 is an oblique perspective figure of one of the microneedles composing the microneedle array according to a reference example.

As shown in FIGS. 5, 6(A), and 6(B), the microneedle array according to the reference example is composed by disposing in a dispersion state a plurality of microneedles (also referred to as "needles" or "fine needles") 60 made of a resin, which each are roughly in a shape of a frustum of a cone (as an example of a tapering shape), on e.g. a flat plate 61 that is an example of a mount made by using the same resin as the microneedles 10 (the microneedles 60 are standing and being disposed according to a preset arranging pattern), and it is something (a medical device) for administering a drug into the body replacing e.g. a conventionally-used syringe. A detailed explanation will be provided below.

Each microneedle 60 is provided with two puncture portions 64 and 65 with a same height each having a flat tip. The puncture portions 64 and 65 each have a part of a side surface of the microneedle 60 as outer surfaces 62 and 63, respectively. Surrounded by inner surfaces 66 and 67 of the puncture portions 64 and 65, a housing section 69 capable of holding a drug is provided. The housing section 69 opens toward the tip side and lateral directions along the axis core of the microneedle 60 and has a central bottom surface 68 that is an example of a bottom surface. One of the both ends of the central bottom surface 68 is contiguous with the base end of the inner surface 66 and the other one is contiguous with the base end of the inner surface 67. The central bottom surface 68 is located on a flat surface orthogonally intersecting (as an example of intersecting) with the axis core of the microneedle 60 at e.g. an intermediate height position $H_M$ along the axis core direction of the microneedle 60. Incidentally, the inner surfaces 66 and 67 forming both flat surfaces of the housing section 69 are provided in a tapering state that gradually widens upwardly and are symmetrical with respect to the axis core of the microneedle 60 as the center.

Although puncture portion tip surfaces 70 and 71 of the puncture portions 64 and 65 are flat, any one of or both of the puncture portion tip surfaces of the two puncture portions may be non-flat with a tip side not being pointed. Also, it can be four same-height puncture portions each having a flat or non-flat tip, which are evenly arranged on the circumference of the microneedle (disposed at circumferential angle positions where the circumference is evenly divided into three or four along a circumferential direction) when viewing the microneedle from above to be provided to each microneedle.

As shown in FIG. 6(A), the lower limit of a height $H_T$ of the microneedle 60 (the height of the puncture portion tip surfaces 70 and 71 of the puncture portions 64 and 65 with respect to the upper surface of the flat plate 61) is 0.1 mm, preferably 0.3 mm. The upper limit of the height $H_T$ is 5.0 mm, preferably 2.0 mm. The lower limit of a base end outer diameter $D_O$ of the microneedle 60 is 0.1 mm, preferably 0.3 mm, and the upper limit of the base end outer diameter $D_O$ is 1.0 mm, preferably 0.6 mm. In a side view, the lower limit of a distance $W_O$ between the tips of the inner surface 66 of the puncture portion 64 and the inner surface 67 of the puncture portion 65 is 0.01 mm, preferably 0.1 mm, and the upper limit of the $W_O$ is 0.9 mm, preferably 0.3 mm. The maximum value of a height $H_D$ of the puncture portions 64 and 65 is 1 mm, preferably not shorter than 0.3 mm and not higher than 0.6 mm. Thus, a height $H_M$ of the central bottom surface 68 (the height position from the upper surface of the flat plate 61) can be decided depending on the amount of the drug to be held by the microneedle 60. The lower limit of the height $H_M$ is 0.1 mm, preferably 0.3 mm, and the upper limit is 4.0 mm, preferably 1.0 mm.

The inner surfaces 66 and 67 of the housing section 69 each have a downward slope from the tips of the puncture portions 64 and 65 toward the central bottom surface 68. The side cross-sectional shape of the housing section 69 is in a trapezoidal shape (an isosceles trapezoidal shape) where the width gets gradually narrower from the tips of the puncture portions 64 and 65 toward the central bottom surface 68. A blade 72 of the puncture portion 64 is continuously formed along a part where the inner surface 66 and the outer surface 62 meet, whereas a blade 73 of the puncture portion is continuously formed along a part where the inner surface 67 and the outer surface 63 meet.

The volume of the housing section 69 is determined by values of the height $H_D$, the distance $W_O$, and a distance $W_B$ between the base ends of the inner surface 66 of the puncture portion 64 and the inner surface 67 of the puncture portion 65. The distance $W_B$ is determined by values of the distance $W_O$ and the angle of each downward slope of the inner surfaces 66 and 67. Since the amount of the drug that the housing section 69 can hold is determined by the volume of the housing section 69, the downward slope angle is set within a range of 1 to 15 degrees such that the distance $W_B$ determined by the needed drug amount can be obtained.

Here, it is possible to improve the puncturability of the puncture portions 64 and 65 by setting the downward slope angle within a range of not smaller than 1 degree and not larger than 5 degrees. Also, it is possible to improve the deformation resistance of the puncture portions 64 and 65 by setting the downward slope angle beyond 5 degrees and not larger than 15 degrees. Incidentally, if the downward slope angle is smaller than 1 degree, it becomes more difficult to demold the microneedles from the injection mold when manufacturing the microneedles by injection molding, and if the downward slope angle is larger than 15 degrees, the puncturability of the microneedles declines. Thus, it is not preferred to set the downward slope angle smaller than 1 degree or larger than 15 degrees.

By setting a maximum value of the height $H_D$ of the puncture portions 64 and 65 to be 1 mm, preferably not shorter than 0.3 mm and not higher than 0.6 mm, breakages of the microneedles 60 can be suppressed, or moreover, be prevented when using the microneedle array (when the microneedles 60 are inserted into the skin). Also, employing this configuration enables the tip of each microneedle 60 (the puncture portion tip surfaces 70 and 71 of the puncture portions 64 and 65 of each microneedle 60) to be present at subcutaneous painless points (within a painless range), so that the pain becomes not to be felt (becomes more difficult to be felt).

With regard to a width t of each of the puncture portion tip surfaces 70 and 71 (the maximum distance between the tip of the outer surface 62 and the tip of the inner surface 66 or the maximum distance between the tip of the outer surface 63 and the tip of the inner surface 67), the lower limit of the width t is 0.005 mm, preferably 0.01 mm, whereas the upper limit of the width t is 0.1 mm, preferably 0.05 mm. By employing this configuration, it is possible to prevent the tip sides of the puncture portions 64 and 65 from getting deformed and broken, and besides, it is possible to maintain the puncturability of the puncture portions 64 and 65 (the tip sides of the puncture portions 64 and 65 can be easily inserted into the skin).

Actions of the microneedle array according to the reference example will subsequently be explained. When pushing the microneedles 60 onto the skin (epidermis), along the outline of each tip of the puncture portions 64 and 65, a slit portion is formed on the surface layer side of the skin. When further pushing the microneedles 60 into the skin, a part of the skin existing between the puncture portions 64 and 65 enters into the housing section 69. This makes it possible to keep at a lower level the increase of the resistance force applied by the skin as the puncture portions 64 and 65 are gradually inserted into the skin, comparing to the conventional microneedle with a tip side of a simple circular cone shape, thereby easily inserting the microneedles 60 into the skin (possible to improve the puncturability of the microneedles 10).

By setting a maximum value of the height $H_D$ of the puncture portions 64 and 65 to be 1 mm, preferably not shorter than 0.3 mm and not higher than 0.6 mm, the drug inside the housing section 69 moves to the dermis (under the epidermis), or otherwise, it is expected that the drug inside the housing section 69 is surely pushed out by the part of the skin that is entering into the housing section 69. This makes it possible to make the drug pushed out from the housing section 69 effectively reach the dermis by using the slit portions formed on the skin, especially parts of the slit portions along the inner surfaces 66 and 67 of the puncture portions 64 and 65.

The housing section 69 is formed between the puncture portions 64 and 65. So, the volume of the housing section 69 can be made larger comparing to the volume of a housing section, which is formed at a central part of the conventional microneedle having a shape of a simple circular cone and along the axis core of the conventional microneedle. Besides, when immersing the microneedles 60 into the drug from the tip side, the air pushed out from inside the housing section 69 by the drug having come into the tip side of the housing section 69 can escape away from the base side (a part having yet to be immersed into the drug) of the housing section 69 that opens toward the lateral directions along the axis core of the microneedle 60, and thus, the drug can surely enter into the housing section 69. This enables the microneedles 60 to hold the predetermined amount of the drug.

Cases where a part or parts of or entirety of each of the above-mentioned embodiments and reference example are combined to configure a microneedle array according to the present invention are also included within the scope of rights of the present invention. For example, the microneedle array may not necessarily be entirely composed of a resin, and it is sufficient that at least the microneedles are composed of a resin. Also, a surface treatment (e.g. roughness degree adjustment and forming a coating layer such as plating) may be applied to each microneedle.

Moreover, although the microneedle array according to the first and second embodiments of the present invention is something (a medical device) for administering a drug into the body replacing a conventionally-used syringe, the microneedle array according to the present invention can be used also for e.g. administering a skin-care serum to the skin or the scalp.

INDUSTRIAL APPLICABILITY

The microneedle array according to the present invention has two or four of the puncture portions around each housing section for the drug, and each puncture portion is in a tapering state where the width gets gradually narrower as it goes up, i.e., toward the puncture direction. This makes it possible to mold a large number of the microneedles by using molding dies, thereby providing the microneedle array at a lower price.

REFERENCE SIGNS LIST

10: microneedle, 11: flat plate, 12, 13: outer surface, 14, 15: puncture portion, 16, 17: inner surface, 18: central bottom surface, 19: housing section, 20, 21: puncture portion tip surface, 22, 23: blade, 24: microneedle, 25: flat plate, 26, 27, 28, 29: outer surface, 30: puncture portion, 30*a*: tip surface, 31: puncture portion, 31*a*: tip surface, 32: puncture portion, 32*a*: tip surface, 33: puncture portion, 33*a*: tip surface, 34, 35, 37, 38, 39, 40, 41: inner surface, 42: central bottom surface, 43: housing section, 44: blade, 45, 46, 47: partial blade, 48: blade, 49, 50, 51: partial blade, 52: blade, 53, 54, 55: partial blade, 56: blade, 57, 58, 59: partial blade, 60: microneedle, 61: flat plate, 62, 63: outer surface, 64, 65: puncture portion, 66, 67: inner surface, 68: central bottom surface, 69: housing section, 70, 71: puncture portion tip surface, 72, 73: blade

The invention claimed is:

1. A microneedle array comprising a plurality of tapering microneedles made of a resin, the microneedles standing and being disposed in a dispersion state on a mount having a flat plate state,
    wherein each microneedle has a substantially conical shape with an open tip side,
    wherein, at the tip side of each of the microneedles, two puncture portions facing each other are provided, the two puncture portions of each microneedle each have a part of a side surface of the respective microneedle as an outer surface, one of the two puncture portions of each microneedle is shorter than an other of the two puncture portions of the respective microneedle, each microneedle includes a housing section capable of holding a drug, the housing section of each microneedle is formed by inner surfaces of the two puncture portions of the respective microneedle facing each other, the housing section of each microneedle opens toward the tip side of the respective microneedle and opens toward the side surface of the respective microneedle in a direction orthogonal to an axis core of the respective microneedle, and the housing section of each microneedle has, at a bottom end, a central bottom surface being in parallel with an upper surface of the mount, and
    wherein each of the inner surfaces of the two puncture portions of each microneedle has a downward slope inclined toward the inner surface of the other of the two puncture portions of the respective microneedle from a tip of the respective puncture portion toward the central bottom surface of the respective microneedle, an angle of the downward slope is within a range of 1 to 15 degrees, and a width between the inner surfaces of the two puncture portions of each microneedle gets narrower as the width goes down from the tip side of the respective microneedle toward the central bottom surface of the respective microneedle.

2. The microneedle array as set forth in claim 1, wherein the tips of the two puncture portions of each microneedle are flat, and are formed in parallel with the upper surface of the mount.

3. A microneedle array comprising a plurality of tapering microneedles made of a resin, the microneedles standing and being disposed in a dispersion state on a mount having a flat plate state,
    wherein each microneedle has a substantially conical shape with an open tip side,
    wherein, at the tip side of each of the microneedles, four puncture portions are provided at positions where each of the microneedles is evenly divided into four in a circumferential direction when viewed from above, the four puncture portions of each microneedle each have a part of a side surface of the respective microneedle as an outer surface, at least one of the four puncture portions of each microneedle has a different height from the others of the four puncture portions of the respective microneedle, each microneedle includes a housing section capable of holding a drug, the housing section of each microneedle is formed among the four puncture portions of the respective microneedle, the housing section of each microneedle opens toward the tip side of the respective microneedle and opens toward the side surface of the respective microneedle between the puncture portions adjacent to each other in the circumferential direction of the respective microneedle, and the housing section of each microneedle has, at a bottom end, a central bottom surface being in parallel with an upper surface of the mount, and
    wherein each of the four puncture portions of each microneedle has inner surfaces facing the inner surfaces of at least two of the other of the four puncture portions to form the housing section of each microneedle, each of the inner surfaces of each of the four puncture portions of each microneedle has a downward slope inclined toward the inner surface of one of the other puncture portions of the respective microneedle from a tip of the respective puncture portion toward the central bottom surface of the respective microneedle, an angle of the downward slope is within a range of 1 to 15 degrees, and a width between the inner surfaces of the four puncture portions of each microneedle gets narrower as the width goes down from the tip side of the respective microneedle toward the central bottom surface of the respective microneedle.

4. The microneedle array as set forth in claim 3, wherein the tips of the four puncture portions of each microneedle are flat, and are formed in parallel with the upper surface of the mount.

\* \* \* \* \*